US011992449B2

(12) United States Patent
Yin et al.

(10) Patent No.: US 11,992,449 B2
(45) Date of Patent: May 28, 2024

(54) HAND MOTION DETECTION DEVICE AND CONTROL METHOD, REHABILITATION DEVICE AND AUTONOMOUS CONTROL SYSTEM

(71) Applicant: Shanghai Siyi Intelligent Technology Co., Ltd., Shanghai (CN)

(72) Inventors: Ganggang Yin, Shanghai (CN); Wudong Wang, Shanghai (CN); Zhongzhe Chen, Shanghai (CN)

(73) Assignee: SHANGHAI SIYI INTELLIGENT TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/355,066

(22) Filed: Jul. 19, 2023

(65) Prior Publication Data

US 2023/0363971 A1 Nov. 16, 2023

Related U.S. Application Data

(63) Continuation of application No. PCT/CN2021/092796, filed on May 10, 2021.

(30) Foreign Application Priority Data

Jan. 22, 2021 (CN) .......................... 202110087810.5

(51) Int. Cl.
*A61H 1/02* (2006.01)
(52) U.S. Cl.
CPC ... *A61H 1/0288* (2013.01); *A61H 2201/5058* (2013.01)
(58) Field of Classification Search
CPC .......... A61H 1/0288; A61H 2201/1238; A61H 2201/1409; A61H 2201/1638;
(Continued)

(56) References Cited

U.S. PATENT DOCUMENTS 6,701,296 B1 * 3/2004 Kramer .................. G06F 1/163
370/545
10,143,403 B2 12/2018 Ban et al.
(Continued)

FOREIGN PATENT DOCUMENTS

CN 106389097 A 2/2017
CN 106618948 A 5/2017
(Continued)

OTHER PUBLICATIONS

China National Intellectual Property Administration, International Search Report, Application No. PCT/CN2021/092796, mailed Sep. 26, 2021, 6 pages.

*Primary Examiner* — Quang D Thanh
(74) *Attorney, Agent, or Firm* — Andrew C. Cheng

(57) ABSTRACT

A hand motion detection device includes a motion detection portion on a finger joint of a first hand. The motion detection portion is configured to generate detection information for feedback of finger joint movement during a stretching movement and a flexion movement of a finger of the first hand so that the motion detection portion can generate in real time the detection information for feedback of the finger joint movement during the stretching movement and the flexion movement of the finger of the first hand. The motion detection portion is connected to a control portion and configured for transmitting the detection information to the control portion, which is adapted to generate an execution instruction according to the detection information so that real-time and accurate acquisition of finger joint motion information of the first hand and timely transmission of the detection information to the control portion can be achieved.

13 Claims, 4 Drawing Sheets

(58) Field of Classification Search
CPC ...... A61H 2201/165; A61H 2201/5025; A61H 2201/5056; A61H 9/0078; A61H 1/0218; A61H 1/0285; A61H 3/00; A61H 2201/1635; A61H 2201/5058; A61H 2205/067; A61H 2230/625; A61B 5/6806; A61B 5/1126; A61B 5/6826; A61B 2505/09; A61B 5/1125; A61B 5/11; A61B 2562/16; A61F 5/0118; A61F 5/013; A63B 23/16; B25J 9/0006; G06F 3/014; A41D 19/0027

See application file for complete search history.

(56) References Cited

U.S. PATENT DOCUMENTS

| | | |
|---|---|---|
| 11,464,450 B2 | 10/2022 | Huang et al. |
| 2012/0157263 A1 | 6/2012 | Sivak et al. |
| 2013/0226350 A1 | 8/2013 | Bergelin et al. |
| 2016/0162022 A1* | 6/2016 | Seth .................. G06F 3/014 345/156 |
| 2018/0303698 A1* | 10/2018 | Wijesundara ........... F15B 15/10 |
| 2018/0364804 A1* | 12/2018 | Hoen ..................... G06F 3/014 |
| 2019/0099123 A1* | 4/2019 | Zambriski ............ A61B 5/7445 |
| 2020/0371591 A1* | 11/2020 | Remaley ................ H02N 13/00 |
| 2021/0081042 A1* | 3/2021 | Baier ................... A61B 5/6806 |
| 2023/0108327 A1 | 4/2023 | Yin et al. |

FOREIGN PATENT DOCUMENTS

| | | |
|---|---|---|
| CN | 107205879 A | 9/2017 |
| CN | 206714926 U | 12/2017 |
| CN | 208426594 U | 1/2019 |
| CN | 109999429 A | 7/2019 |
| CN | 110013219 A | 7/2019 |
| CN | 110478195 A | 11/2019 |
| CN | 110801372 A | 2/2020 |
| CN | 111249112 A | 6/2020 |
| CN | 211584109 U | 9/2020 |
| JP | 2018029729 A | 3/2018 |
| KR | 20170086238 A | 7/2017 |
| KR | 20180072264 A | 6/2018 |
| KR | 20180134083 A | 12/2018 |
| KR | 102131065 B1 | 7/2020 |
| WO | 2015114601 A1 | 8/2015 |

* cited by examiner

HAND MOTION DETECTION DEVICE AND CONTROL METHOD, REHABILITATION DEVICE AND AUTONOMOUS CONTROL SYSTEM

FIELD OF TECHNOLOGY

The present disclosure relates to the technical field of finger rehabilitation training, in particular to a hand motion detection device and control method, a rehabilitation device and an autonomous control system.

BACKGROUND

According to the statistic, there are more than 10 million stroke patients in China at present, and the number of new patients exceeds 2 million every year. Hand dysfunction after stroke is the most common and difficult to recover. Patients with hand dysfunction need long-term hand rehabilitation training to restore hand function. With the development of rehabilitation robot technology, more and more hand functional rehabilitation robots are used in the rehabilitation of patients with hand dysfunction.

The patent published No. KR1020180072264A discloses a hand rehabilitation training system and a training method, the patent published No. KR1020180134083A discloses a ball type hand joint rehabilitation apparatus and a rehabilitation system including the same, and the patent published No. CN208426594U discloses a gripper for resisting hand scar contracture. All the three inventions adopt the way of clenching fists and pressing air bags to collect hand motion information, which has the problems of low accuracy of collecting finger joint motion information, inability to collect real-time finger joint motion information, and inability to collect single finger joint motion. However, in the prior art, the cost of collecting motion information of a single finger joint by using angle sensors is relatively high.

The patent published No. CN110478195A discloses a sensor device and an integrated finger joint rehabilitation glove. The sensor device comprises a finger portion which is adapted to be sleeved on a finger of a user and is bent along with the bending of the finger of the user. The finger portion is provided with a finger sensor, and the finger sensor is used for transmitting the action of the finger portion to the controller; the controller sends a trigger signal after receiving the signal sent by the finger sensor, wherein the controller is connected to the finger sensor through a signal line. In this way, the control signal is generated according to the user's finger, which can be the patient's family member or even the patient himself, so as to better understand the actual situation of the patient and generate more accurate control signals. However, the patent has the following defects: (1) the permanent magnet will have the risk of weakening the magnetic force, eliminating the magnetism due to external reasons, and falling off the magnet; (2) because the magnetism will cause electromagnetic interference to external equipment or be affected by the outside world, it has some restrictions on the trial scene and use conditions; (3) it is heavy and causes a heavy load to users, and will affect finger movement; (4) a group of permanent magnets and Hall switches can only detect a single joint, if the user wants to detect the movement of multiple joints of a single finger, multiple groups of permanent magnets and Hall switches are required, which are heavy and will affect the movement of fingers and cannot detect multiple joints.

Therefore, it is necessary to provide a novel hand motion detection device and a control method, a rehabilitation device and an autonomous control system to solve the above problems in the prior art.

SUMMARY

The present disclosure aims to provide a hand motion detection device, a control method, a rehabilitation device and an autonomous control system so as to realize real-time and accurate acquisition of motion information of finger joints of a first hand.

In order to achieve the above object, the hand motion detection device of the present disclosure comprises a motion detection portion arranged on a finger joint of a first hand and configured for generating detection information for feedback of finger joint movement during a stretching movement and a flexion movement of a finger of the first hand, the motion detection portion being connected to a control portion, the motion detection portion configured for transmitting the detection information to the control portion, and the control portion adapted to generate an execution instruction according to the detection information.

The hand motion detection device of the present disclosure has the beneficial effect that the motion detection portion is arranged on a finger joint of a first hand and generates detection information for feedback of finger joint movement during the stretching movement and the flexion movement of a finger of the first hand so that the motion detection portion can generate in real time the detection information for feedback of the finger joint movement during the stretching movement and the flexion movement of the finger of the first hand. The motion detection portion is connected to a control portion, the motion detection portion is configured for transmitting the detection information to the control portion, and the control portion is adapted to generate an execution instruction according to the detection information so that real-time and accurate acquisition of finger joint motion information of the first hand and timely transmission of the detection information to the control portion can be achieved.

Preferably, the motion detection portion comprises a first detection unit and a second detection unit arranged separately, the first detection unit is configured to touch the second detection unit when the finger of the first hand is bent, thereby triggering the generation of the detection information. The present disclosure has the beneficial effect that the first detection unit and the second detection unit come into contact with each other as the finger of the first hand is bent so as to generate the detection information, thereby achieving real-time and accurate acquisition of the motion information of the finger joint of the first hand.

Preferably, the motion detection portion is provided across at least one finger joint, and the detection information is generated during the stretching movement and the flexion movement of the at least one finger joint. The present disclosure has the beneficial effect that the motion detection portion can detect the motion information of at least one finger joint.

Preferably, at least one finger of the first hand is provided with a motion detection portion, and a single finger is provided with at least one motion detection portion. The present disclosure has the beneficial effect that the motion detection portion can detect the motion information of the finger joint of at least one finger of the first hand.

Preferably, each of the finger joints is provided with a plurality of motion detection portions. The present disclosure has the beneficial effect that the accuracy of detecting the motion information of the finger joint of the first hand can be improved, and the motion angles of the finger joint of the first hand in multiple directions, such as the angle of adduction motion and the angle of abduction motion of the metacarpophalangeal joint, can be detected.

Preferably, the hand motion detection device further comprises a wearable portion, the wearable portion being in a shape of a glove and comprising a finger portion, and the motion detection portion is arranged on the finger portion. The present disclosure has the beneficial effect that the motion detection portion is arranged on the wearable portion can effectively prevent the motion detection portion from falling off the hand of the user. This is convenient for the user to use the hand motion detection device, and is especially suitable for people with insensitive hands.

Preferably, the finger portion is provided with an accommodating portion, and the motion detection portion is arranged within the accommodating portion. The present disclosure has the beneficial effect that the device is simple in setting and can effectively prevent the relative sliding of the motion detection portion with respect to the finger portion of the wearable portion, and it ensures that the motion detection portion can move together with the finger of the user, and is convenient to disassemble the motion detection portion from the finger portion and easy to clean the wearable portion.

Preferably, the motion detection portion is fixed to the finger portion by any one of glue, a hook and loop fastener, a magnet, a stitch, buckle, a finger cuff and a strap. The present disclosure has the beneficial effect that the relative sliding of the motion detection portion with respect to the finger portion of the wearable portion can be effectively prevented, and it is guaranteed that the motion detection portion can move together with the finger of the user.

Preferably, the first detection unit comprises a first conductive adhesive layer, the second detection unit comprises a second conductive adhesive layer, the first conductive adhesive layer and the second conductive adhesive layer are not in contact with each other and are respectively arranged on opposite inner side walls of an elastic housing, and when the finger joint of the first hand is in a flexion state, the first conductive adhesive layer and the second conductive adhesive layer can be in contact with each other so as to generate the detection information. The present disclosure has the beneficial effect that the first detection unit and the second detection unit have the simple structure, great design, low cost with the first conductive adhesive layer, the second conductive adhesive layer and the elastic housing having good flexibility, and it is easy for the first conductive adhesive layer and the second conductive adhesive layer to bend along with the stretching movement and flexion movement of the fingers of the first hand.

Preferably, the first conductive adhesive layer and the second conductive adhesive layer are made of conductive adhesive. The present disclosure has the beneficial effect that the first conductive adhesive layer and the second conductive adhesive layer have the simple structure, ingenious design and low cost.

Preferably, the first conductive adhesive layer and the second conductive adhesive layer comprise conductive adhesive and a wire embedded in the conductive adhesive. The present disclosure has the beneficial effects of further ensuring the conductive effect of the conductive adhesive.

Further preferably, the control portion and the motion detection portion are electrically connected by the wire. The present disclosure has the beneficial effect that it is easy to connect the control portion to the motion detection portion by utilizing the wire, the connection is simple, the cost is low, and the information transmission is stable.

Preferably, one end of the elastic housing is further provided with a conductive element, upper and lower end faces of the conductive element are respectively in contact with the first conductive adhesive layer and the second conductive adhesive layer, and the control portion and the motion detection portion are electrically connected by the conductive element. The present disclosure has the beneficial effect that the upper and lower end faces of the conductive element are respectively in contact with the first conductive adhesive layer and the second conductive adhesive layer, so as to not only increase the support strength of the head end of the motion detection portion, but also make the electric information collection more sensitive.

Preferably, the control method of the hand motion detection device comprises:

S1, generating, by a motion detection portion, detection information for feedback of finger joint motion during a stretching movement and a flexion movement of a finger of a first hand, and transmitting the detection information to a control portion; and S2, generating, by the control portion, an execution instruction according to the detection information. The present disclosure has the beneficial effect of realizing real-time and accurate acquisition of motion information of finger joints of the first hand.

Preferably, the present disclosure also provides a rehabilitation device, which comprises the hand motion detection device to collect detection information, and the rehabilitation device further comprises an air pressure regulating assembly and a wearable training portion, the wearable training portion is provided with a pneumatic adjustable component that can expand and contract freely, and the air pressure regulating assembly is connected to the pneumatic adjustable component that can expand and contract freely; and the air pressure regulating assembly is connected to a control portion, and the control portion is configured to control the air pressure regulating assembly to regulate the air pressure in the pneumatic adjustable component that can expand and contract freely according to the detection information, so that the wearable training portion is changed between a flexion condition and a stretching condition so as to achieve hand mirror training of a second hand.

The rehabilitation device of the present disclosure has the beneficial effect that the hand motion detection device can collect the motion information of the finger joint of the first hand, and the control portion can control the air pressure regulating assembly to regulate the air pressure in the pneumatic adjustable component that can expand and contract freely according to the detection information, so that the wearable training portion can change between the flexion condition and the stretching condition to realize the hand mirror training of the second hand, so that the condition of the second hand can be regulated through the condition of the first hand, that is, the information of the wearable training portion can be controlled according to the finger of the user, and can be the family member of the patient or even the patient himself, so that the rehabilitation training time, action and intensity of the second hand can be regulated autonomously, and the wearable training portion can be better regulated to meet the rehabilitation training requirements of the second hand.

Preferably, the present disclosure also provides an autonomous control system comprising an executing portion and a hand motion detection device, the executing portion is connected to the control portion.

The autonomous control system of the present disclosure has the beneficial effect that the motion information of the finger joint of the first hand is fed back by the movement of the executing portion according to the execution instruction, so that the user can not only get the training feedback result in real time, but also improve the enthusiasm of the user for self-training, and the training compliance is high, and the flexible control of the executing portion can be realized autonomously.

Preferably, the executing portion comprises a driving unit configured for driving an image to move or a sound to change or a game to run according to a motion execution instruction, the image, the sound and the game being stored in a terminal device. The present disclosure has the beneficial effect that the executing portion can drive the image to move or a sound to change or a game to run according to a motion execution instruction so that the user can autonomously regulate the collection of the motion information of the finger joints of the first hand according to the feedback result to carry out the hand autonomous training, the flexibility of the autonomous training is higher, the actual situation of the user is more appropriate, and the training effect is improved. Moreover, by driving the image to move or the sound to change or the game to run to feedback the motion information of the finger joints of the first hand, the user can get the training feedback result in real time, the training effect is more intuitive, and the completion degree of the hand action of the patient can be accurately reflected, driven by the fun of the game, the user is willing to carry out autonomous training, the training compliance is high, and the training effect is improved.

DESCRIPTION OF THE EMBODIMENTS

In order to make objectives, technical solutions, and beneficial effect of the disclosure clearer, the technical solutions in the present disclosure are described clearly and completely in the following with reference to accompanying drawings in the embodiments of the disclosure. Apparently, the described embodiments are only part rather than all of the embodiments of the disclosure. Based on the embodiments of the present disclosure, all the other embodiments obtained by those of ordinary skill in the art without inventive effort are within the scope of the present disclosure. Unless otherwise mentioned, all technical and scientific terms used herein have the same meaning as commonly understood by one of ordinary skill in the art to which the present disclosure belongs. The term "including" and the like as used herein means that the elements or articles appearing before the term encompass the enumerated elements or articles appearing after the term and their equivalents, without excluding other elements or articles.

Figure 1:
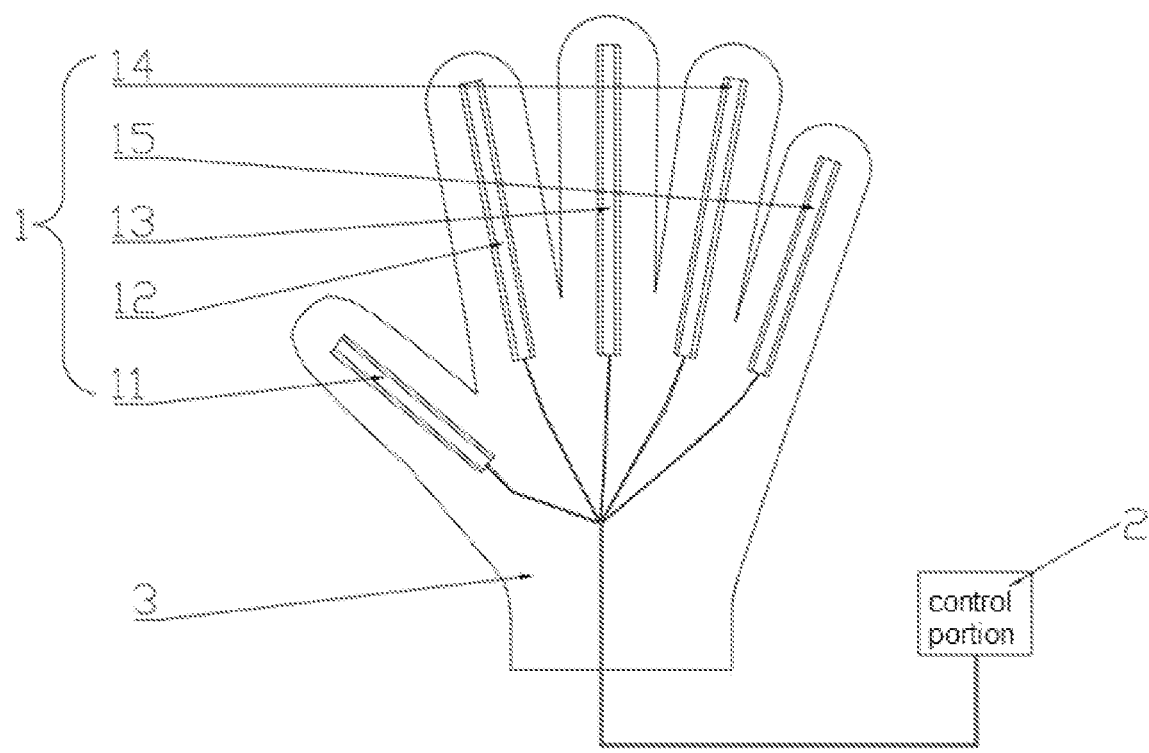
FIG. 1 is a schematic structural diagram of a hand motion detection device in some embodiments of the present disclosure.

FIG. 1 is a schematic structural diagram of a hand motion detection device in some embodiments of the present disclosure.

Aiming at the problems existing in the prior art, the embodiments of the present disclosure provide a hand motion detection device, as shown in FIG. 1, which includes a motion detection portion 1 arranged on a finger joint of a first hand and generating detection information for feedback of finger joint movement during a stretching movement and a flexion movement of a finger of the first hand, the motion detection portion 1 is connected to a control portion 2, the motion detection portion 1 is configured to transmit the detection information to the control portion 2, and the control portion 2 is configured to generate an execution instruction according to the detection information, so that the motion detection portion can generate in real time the detection information for feedback of the finger joint movement during the stretching movement and flexion movement of the finger of the first hand, so that real-time and accurate acquisition of finger joint motion information of the first hand and timely transmission of the detection information to the control portion can be achieved.

In some embodiments of the present disclosure, the control portion is a part of the hand motion detection device, and the motion detection portion is connected to the control portion through a wired or wireless mode.

In some embodiments of the present disclosure, the control portion is sleeved on the wrist of the user through a strap and other structures.

In some embodiments of the present disclosure, the control portion is arranged in the palm portion or the palm center of the first hand, preferably the palm portion, by pasting or binding, etc., so as to prevent the user from affecting the finger flexion movement.

In some embodiments of the present disclosure, the control portion may be a component configured with a device used in conjunction with the hand motion detection device, and the motion detection portion and the control portion are connected by a wired or wireless mode.

In some embodiments of the present disclosure, the motion detection portion comprises a first detection unit and a second detection unit arranged separately or spaced apart from each other, when the finger of the first hand is bent, the first detection unit touches with the second detection unit so as to trigger the generation of the detection information, the first detection unit and the second detection unit come into contact with each other under the finger bending of the first hand so as to generate the detection information, thereby achieving real-time and accurate acquisition of the motion information of the finger joint of the first hand. The finger bending of the first hand includes that the finger is in a flexion state or the finger undergoes a flexion change, that is, a non-straightened state.

In some embodiments of the present disclosure, the motion detection portion comprises a first detection unit and a second detection unit arranged separately or spaced apart from each other. When the finger of the first hand is in a straightened state, the first detection unit touches the second detection unit so as to trigger the generation of the detection information. When the finger of the first hand is in a non-straightened state, the first detection unit is not in contact with the second detection unit, and no the detection information is generated. However, in this way, it is difficult to make the structure of the motion detection portion, and only when the finger of the first hand is in the straightened state, the first detection unit touches the second detection unit to generate the detection information, that is, only the change information from the bending state to the straightened state of the finger can be detected, and the detection information of feedback of finger joint movement generated during the finger stretching movement and the flexion movement cannot be detected. Therefore, the detection range of this embodiment is relatively small, and the practical application benefits are not significant.

In some embodiments of the present disclosure, the first detection unit touches the second detection unit so as to trigger the generation of different detection information according to the flexion angle change of the finger joint and send the detection information to the control portion.

In some embodiments of the present disclosure, the detection information includes any one of electrical information, magnetic information, and optical information.

In some embodiments of the present disclosure, the detection information includes at least one of a current, a voltage, an inductance, and a resistance.

In some specific embodiments of the present disclosure, the detection information includes current information and resistance information, when the finger joint of the first hand is in a flexion state or flexion changes, the motion detection portion is deformed with the motion flexion of the finger joint of the first hand, and the first detection unit and the second detection unit contact with each other to generate current information. When the finger joint of the first hand is in the straightened state, the motion detection portion is straightened with the finger joint movement of the first hand, and the first detection unit and the second detection unit are not in contact. And when the flexion angle of the finger joint of the first hand is changed, the flexion angle of the motion detection portion is also changed, and the contact area between the first detection unit and the second detection unit is changed, resulting in the change of the generated resistance value information. When the finger joint of the first hand makes flexion movement, the motion detection portion makes flexion change accordingly, and the contact area between the first detection unit and the second detection unit gradually increases, resulting in the generated resistance value gradually decreases, and when the finger joint of the first hand is stretched, the motion detection portion is changed accordingly, and the contact area between the first detection unit and the second detection unit is gradually reduced, resulting in a gradually larger resistance value.

In some embodiments of the present disclosure, when the first detection unit and the second detection unit contact each other, the resistance value of the motion detection portion changes in the range of 10-1000 ohms, which is convenient for real-time reaction of the flexion angle of the finger joint. The flexion angle value of the finger joint is different, and the resistance value of the motion detection portion is different, and this is convenient for the control portion to analyze and process the resistance value information to obtain the flexion angle value of the finger joint.

In some embodiments of the present disclosure, the resistance value of the motion detection portion varies in the range of 300-800 ohms, specifically, the resistance value of the motion detection portion may be 350 ohms, 400 ohms, 500 ohms, 600 ohms, 650 ohms, 700 ohms, 750 ohms, etc. depending on the flexion angle value of the finger joint.

In some embodiments of the present disclosure, the resistance value of the motion detection portion varies in the range of 30-150 ohms, specifically, the resistance value of the motion detection portion may be 35 ohms, 40 ohms, 60 ohms, 120 ohms, 130 ohms, 140 ohms, etc. depending on the flexion angle value of the finger joint.

In some embodiments of the present disclosure, the resistance value of the motion detection portion varies in the range of 50-100 ohms, specifically, the resistance value of the motion detection portion may be 55 ohms, 65 ohms, 70 ohms, 75 ohms, 80 ohms, 85 ohms, 90 ohms, etc. depending on the flexion angle value of the finger joint.

In some embodiments of the present disclosure, the motion detection portion is arranged on the finger of the first hand by pasting, binding or finger cuff, and the motion detection portion is arranged across the finger joint of the first hand.

In some embodiments of the present disclosure, the motion detection portion is arranged on the finger belly surface or the finger belly back surface of the finger of the first hand. The motion detection portion is arranged in various positions, and can be selected to be arranged on the finger belly surface or the finger belly back surface of the finger of the first hand according to the actual situation. The motion detection portion has a simpler structure to fit the finger belly surface or the finger belly back surface of the finger of the first hand, and it is helpful to generate detection information along with the stretching movement and the flexion movement of the finger of the first hand so as to improve the accuracy of motion information detection of the finger joint of the first hand.

In the embodiments of the present disclosure, the finger belly back surface refers to surface of the finger which is in a same plane as the back of the hand, i.e., the side on which the finger has a fingernail cover, the finger belly surface refers to the surface on the finger which is in the same plane as the palm of the hand, i.e., the side opposite to the finger belly back surface, and the first hand is the left hand or the right hand of the user.

In some embodiments of the present disclosure, referring to FIG. 1, the hand motion detection device further includes a wearable portion 3, the wearable portion 3 being in a shape of a glove and comprising a finger portion, and the motion detection portion 1 is arranged on the finger portion. The motion detection portion 1 is arranged on the wearable portion 3, and this can effectively prevent the motion detection portion 1 from falling off the hand of the user and is convenient for the user to use the hand motion detection device, and is especially suitable for people with insensitive hands. In some other preferred embodiments of the present disclosure, the motion detection portion 1 is provided on the belly surface or the back surface of the finger belly.

In some embodiments of the present disclosure, when the control portion is a part of the hand motion detection device, the control portion is arranged at the palm portion or the palm center of the wearable portion.

In some embodiments of the present disclosure, the finger portion is provided with an accommodating portion, and the motion detection portion is arranged in the accommodating portion, which is simple in setting, can effectively prevent the relative sliding of the motion detection portion with respect to the finger portion of the wearable portion, It ensures that the motion detection portion can move together with the finger of the user, and is convenient to disassemble the motion detection portion from the finger portion and easy to clean the wearable portion. In some embodiments of the present disclosure, the accommodating portion is of a mounting bag structure, and the mounting bag is provided with an opening for inserting the data acquisition device into the mounting bag.

In some embodiments of the present disclosure, the wearable portion further includes a suture thread configured for sewing and fixing an edge of the accommodating portion to the finger portion of the wearable glove, and sewing and fixing the accommodating portion to the finger portion of the wearable portion by the suture thread is convenient, simple, firm and durable, and low in cost.

In some embodiments of the present disclosure, the motion detection portion is fixed to the finger portion by any one of glue, hook and loop fastener, magnet, stitch, buckle, finger cuff and strap, the relative sliding of the motion detection portion with respect to the finger portion of the wearable portion can be effectively prevented, and the motion detection portion can be guaranteed to move together with the finger of the user.

In some embodiments of the present disclosure, the wearable portion may also be a strap structure, or other structure capable of fixing the motion detection portion to the finger portion, such as a cloth strip, a rope, a thread, a finger cuff, etc.

In some embodiments of the present disclosure, there are a plurality of motion detection portions, and the motion detection portions are provided for each single finger of the first hand, so that the motion detection portions can respectively detect the motion information of the finger joints of the single fingers.

In some embodiments of the present disclosure, at least one finger of the first hand is provided with the motion detection portion, and a single finger is provided with at least one of the motion detection portions, so that the motion detection portion can detect the motion information of the finger joint of at least one finger of the first hand.

In some embodiments of the present disclosure, the motion detection portion is provided with a plurality of single fingers respectively arranged on the first hand, and the motion detection portion is connected in parallel and respectively connected to the control portion to respectively detect the detection information generated during the stretching movement and the flexion movement of the single finger joint, so that the motion detection portion can respectively detect the motion information of the finger joint of the single finger.

In some embodiments of the present disclosure, referring to FIG. 1, five motion detection portion 1 are provided, namely a first motion detection portion 11, a second motion detection portion 12, a third motion detection portion 13, a fourth motion detection portion 14 and a fifth motion detection portion 15. The five motion detection portions are respectively connected to the control portion. The first motion detection portion 11 is arranged abutting against the surface of the thumb to collect motion information of the finger joint of the thumb and transmits the motion information to the control portion. The second motion detection portion 12 fits the index finger to collect motion information of the finger joint of the index finger and then transmits the motion information to the control portion. The third motion detection portion 13 fits the middle finger to collect motion information of the finger joint of the middle finger and transmits the motion information to the control portion. The fourth motion detection portion 14 fits the ring finger to collect motion information of the finger joint of the ring finger and transmits the motion information to the control portion. The fifth motion detection portion 15 fits the little finger to collect motion information of the finger joint of the little finger and transmits the motion information to the control portion.

In some embodiments of the present disclosure, a plurality of motion detection portions are respectively arranged on different parts or locations of a single finger of the first hand, and the motion detection parts are connected in series and connected to the control portion, so as to generate the detection information and transmit it to the control portion when any one of the finger joints is detected to perform the stretching movement and the flexion movement.

In some embodiments of the present disclosure, the motion detection portion is arranged across at least one finger joint, and the detection information is generated during the stretching movement and the flexion movement of the at least one finger joint, so that the motion detection portion can detect the motion information of at least one finger joint.

Figure 2:
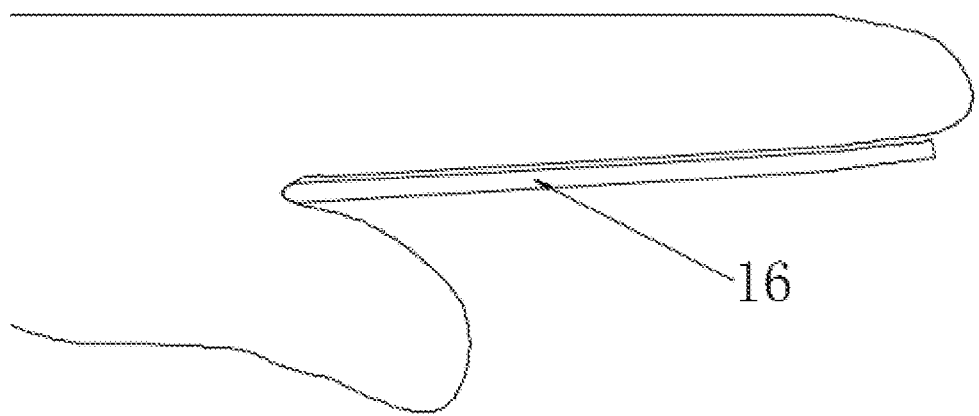
FIG. 2 is a schematic structural diagram of a motion detection portion arranged on a finger in some embodiments of the present disclosure.

FIG. 2 is a schematic structural diagram of a motion detection portion arranged on a finger in some embodiments of the present disclosure.

In some embodiments of the present disclosure, referring to FIG. 2, one motion detection portion is provided as a sixth motion detection portion 16. One end of the sixth motion detection portion 16 crosses the distal interphalangeal joint and fits it, the other end thereof crosses the metacarpophalangeal joint and fits it, and the middle part thereof crosses the proximal interphalangeal joint and fits it so as to detect the motion of the distal interphalangeal joint, the proximal interphalangeal joint and the metacarpophalangeal joint. That is, the sixth motion detection portion 16 simultaneously detects the motion of all the entire finger joints so as to detect the overall motion state of the entire finger, and when any of the distal interphalangeal joint, proximal interphalangeal joint, or metacarpophalangeal joint is stretched, the sixth motion detection portion 160 will then generate the detection information and send it to the control portion.

In some embodiments of the present disclosure, referring to FIG. 2, the motion detection portion 16 is arranged on the finger belly surface of the finger of the first hand, and the motion detection portion 16 is more simple to fit the finger belly surface of the finger of the first hand, and is helpful for the motion detection portion to generate the detection information during the stretching movement and the flexion movement of the finger of the first hand, so as to improve the accuracy of motion information detection of finger joints of the first hand.

Figure 3:
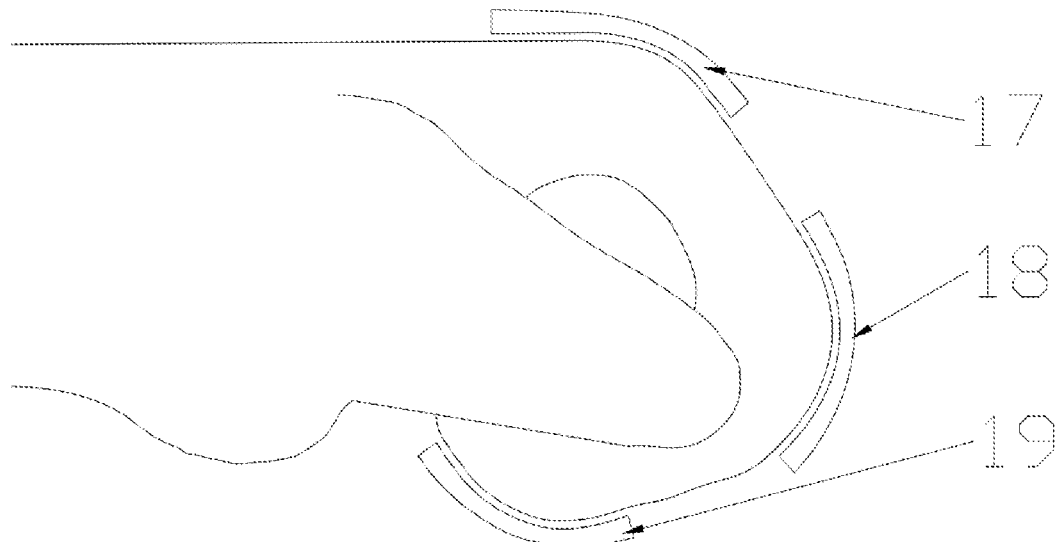
FIG. 3 is a schematic structural diagram of a motion detection portion arranged on a finger in yet another embodiments of the present disclosure.

FIG. 3 is a schematic structural diagram of a motion detection portion arranged on a finger in yet another embodiments of the present disclosure.

In some embodiments of the present disclosure, referring to FIG. 3, there are three motion detection portions, namely, a seventh motion detection portion 17, an eighth motion detection portion 18 and a ninth motion detection portion 19. Each motion detection portion only detects the motion of one finger joint, and each motion detection portion is independent of each other, so that the motion information of the finger joint collected respectively does not affect each other. The seventh motion detection portion 17 crosses the distal interphalangeal joint and is arranged to fit it. The seventh motion detection portion 17 generates detection information during the stretching movement and the flexion movement of the distal interphalangeal joint so as to collect the motion information of the distal interphalangeal joint. The eighth motion detection portion 18 is arranged across the proximal interphalangeal joint and fitted together, and the eighth motion detection portion 18 generates detection information during the stretching movement and flexion movement of the proximal interphalangeal joint so as to collect motion information of the proximal interphalangeal joint. The ninth motion detection portion 19 is provided across and abutting against the metacarpophalangeal joint, and the ninth motion detection portion 19 generates detection information during the stretching and flexing movements of the metacarpophalangeal joint so as to collect motion information of the metacarpophalangeal joint.

In some embodiments of the present disclosure, referring to FIG. 3, the seventh motion detection portion 17, the eighth motion detection portion 18 and the ninth motion detection portion 19 are all provided on the finger belly back surface of the first hand, and the motion detection portion is more simple to fit on the finger belly back surface of the first hand, and is helpful for the motion detection portion to generate detection information during the stretching movement and the flexion movement of the finger of the first hand so as to improve the accuracy of motion information detection of the finger joint of the first hand.

In some embodiments of the present disclosure, the seventh motion detection portion 17, the eighth motion detection portion 18 and the ninth motion detection portion 19 are connected in parallel and are respectively connected to the control portion so as to detect the detection information generated during the stretching and flexing movements of a single finger joint, respectively.

In some embodiments of the present disclosure, the seventh motion detection portion 17, the eighth motion detection portion 18 and the ninth motion detection portion 19 are connected in series and are connected to the control portion through a general wire so as to generate the detection information and then transmit it to the control portion upon detection of the stretching and flexion of any finger joint.

In some embodiments of the present disclosure, each finger joint is provided with a plurality of motion detection portions, thereby improving the accuracy of motion information detection of the finger joint of the first hand, as it likes a finger joint is provided with one motion detection portion on the finger belly back surface and the finger belly surface of the finger respectively.

In some other preferred embodiments of the present disclosure, each of the finger joints is provided with a plurality of the motion detection portions to detect motion angles of the finger joints in a plurality of directions, such as the motion detection portions provided on a finger side of the metacarpophalangeal joint, the finger side being a finger side between a finger belly surface and a finger belly back surface, to detect an angle of adduction motion and an angle of abduction motion of the metacarpophalangeal joint.

In some specific embodiments of the present disclosure, the first hand of the user wears the hand motion detection device, and the finger metacarpophalangeal joint of the first hand is provided with the motion detection portion, which is preferably arranged across the metacarpophalangeal joint and on the finger side of the metacarpophalangeal joint. When the finger joint of the first hand is in a straightened state, the motion detection portion is stretched along with the stretching movement of the finger joint of the first hand, and the first detection unit and the second detection unit do not contact. When the finger moves and the metacarpophalangeal joint rotates, the first detection unit and the second detection unit are relatively bent and contacted with each other to generate detection information. As the rotation angle of the metacarpophalangeal joint increases, the contact area of the first detection unit and the second detection unit increases, and the generated detection information changes. In some embodiments of the present disclosure, the detection information is resistance information, according to which the rotation angle of the metacarpophalangeal joint can be obtained as the contact area of the first detection unit and the second detection unit increases so as to generate resistance information with a reduced resistance value.

In some embodiments of the present disclosure, the first detection unit comprises a first conductive adhesive layer, the second detection unit comprises a second conductive adhesive layer, the first conductive adhesive layer and the second conductive adhesive layer are not in contact with each other and are separately and respectively arranged on opposite inner side walls of an elastic housing. When the finger joint of the first hand is in the straightened state, the first conductive adhesive layer and the second conductive adhesive layer are not in contact with each other. When the finger joint of the first hand is in a flexion state, the first conductive adhesive layer and the second conductive adhesive layer are in contact with each other to generate the detection information, and it is a simple structure, ingenious design, low cost, good flexibility for the first conductive adhesive layer, the second conductive adhesive layer and the elastic housing, and is easy to bend along with the stretching movement and the flexion movement of the fingers of the first hand.

Figure 4:
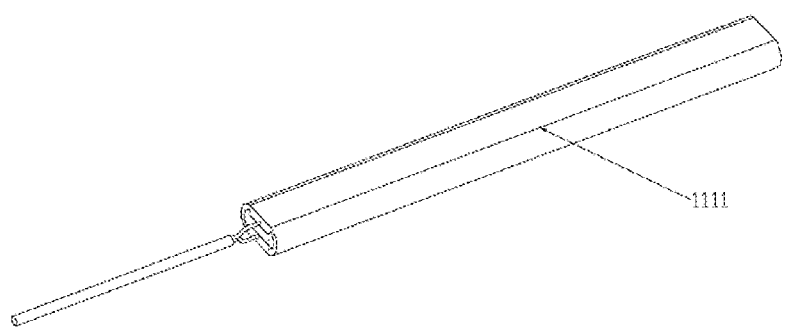
FIG. 4 is a schematic structural diagram of the motion detection portion in some embodiments of the present disclosure.
Figure 5:
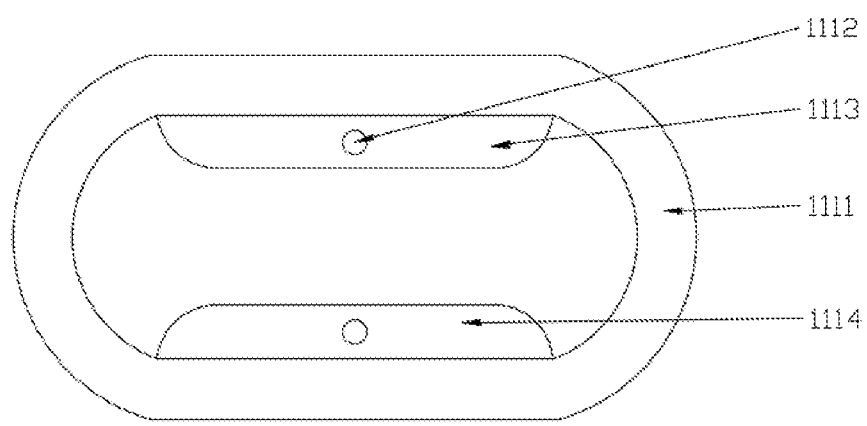
FIG. 5 is a side view of the motion detection portion in some embodiments of the present disclosure.

FIG. 4 is a schematic structural diagram of the motion detection portion in some embodiments of the present disclosure; FIG. 5 is a side view of the motion detection portion in some embodiments of the present disclosure.

In some embodiments of the present disclosure, referring to FIGS. 4 and 5, the first detection unit includes a first conductive adhesive layer 1113, the second detection unit includes a second conductive adhesive layer 1114, the first conductive adhesive layer 1113 and the second conductive adhesive layer 1114 are not in contact with each other and are respectively arranged on the opposite inner side walls of the elastic housing 1111. The first conductive adhesive layer 1113 and the second conductive adhesive layer 1114 both include conductive adhesive and a wire 1112 embedded in the conductive adhesive, the control portion (not shown) and the motion detection portion are electrically connected by the wire 1112, and the wire 1112 is connected to the control portion (not shown) by the connecting wires, so that the connection mode is simple, the cost is low and the information transmission is stable. In some other preferred embodiments of the present disclosure, the wire 1112 is a metal conductive wire. In some other further preferred embodiments of the present disclosure, the wire 1112 is a copper wire.

Figure 6:
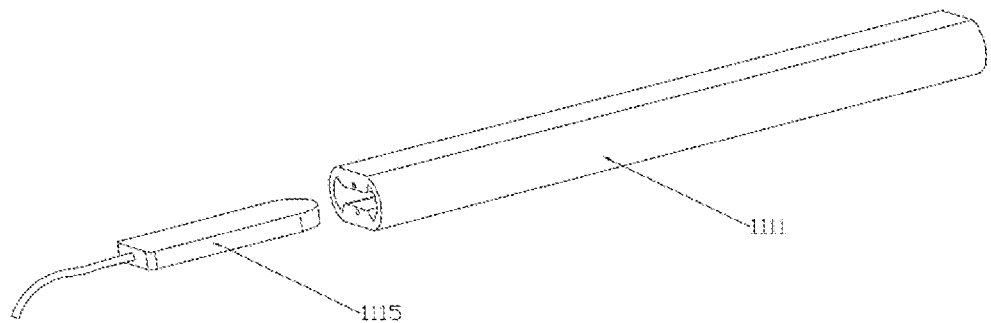
FIG. 6 is a schematic structural diagram of the motion detection portion in yet another embodiments of the present disclosure.

FIG. 6 is a schematic structural diagram of the motion detection portion in yet another embodiments of the present disclosure.

In other embodiments of the present disclosure, referring to FIG. 5 and FIG. 6, the difference between FIG. 6 and FIG. 4 is that one end of the elastic housing 1111 is also provided with a conductive element 1115, the upper and lower end faces of the conductive element 1115 are respectively in contact with the first conductive adhesive layer 1113 and the second conductive adhesive layer 1114, the control portion (not shown) is electrically connected to the motion detection portion by the conductive element 1115, the conductive element 1115 is connected to the control portion (not shown) by a connecting wire, and the upper and lower end faces of the conductive element 1115 are respectively in contact with the first conductive adhesive layer 1113 and the second conductive adhesive layer 1114. Thus, this not only increases the support strength of the head end of the motion detection portion, but also makes the electrical information collection more sensitive. In some other preferred embodiments of the present disclosure, the conductive element is a head terminal.

In further some embodiments of the present disclosure, the first detection unit comprises a first conductive adhesive layer 1113, the second detection unit comprises a second conductive adhesive layer 1114, the first conductive adhesive layer 1113 and the second conductive adhesive layer 1114 are not in contact with each other and are respectively arranged on the opposite inner side walls of the elastic housing 1111, the first conductive adhesive layer 1113 and the second conductive adhesive layer 1114 are both made of conductive adhesive, one end of the elastic housing 1111 is also provided with a conductive element 1115, the upper and lower end faces of the conductive element 1115 are respectively in contact with the first conductive adhesive layer 1113 and the second conductive adhesive layer 1114, and the control portion (not shown) and the motion detection portion are electrically connected by the conductive element 1115. The conductive element 1115 is connected to the control portion (not shown) by the connecting wire.

Specifically, the detection information includes current information and resistance information. When the finger joint of the first hand is in a flexion state or makes the flexion movement, the corresponding motion detection portion flexes along with the finger joint movement of the first hand, the elastic housing 1111 is deformed, and the first conductive adhesive layer 1113 and the second conductive adhesive layer 1114 contact each other to generate current information. When the finger joint of the first hand is in the straightened state, the motion detection portion is straightened along with the movement of the finger joint of the first hand, the elastic housing 1111 springs back and straightens, and the first conductive adhesive layer 1113 and the second conductive adhesive layer 1114 do not contact with each other. When the flexion angle of the finger joint of the first hand is changed, the flexion angle of the motion detection portion is also changed, and the contact area between the first conductive adhesive layer 1113 and the second conductive adhesive layer 1114 is changed, resulting in a change in the generated resistance value information. When the finger joint of the first hand is flexed, the motion detection portion is flexed accordingly, and the contact area between the first conductive adhesive layer 1113 and the second conductive adhesive layer 1114 is gradually increased, resulting in a gradually reduced resistance value. And when the finger joint of the first hand is stretched, the motion detection portion is changed accordingly, and the contact area between the first conductive adhesive layer 1113 and the second conductive adhesive layer 1114 is gradually reduced, resulting in a gradually increased resistance value.

In some embodiments of the present disclosure, the elastic housing is made of silicone rubber, and the silicone rubber is easy to deform, so that when the finger joint of the first hand is flexed, the first conductive adhesive layer and the second conductive adhesive layer are easy to contact with each other, thus ensuring the sensitivity of motion information detection of the finger joint of the first hand.

In some embodiments of the present disclosure, at least one surface of the elastic housing is a concave-convex surface, that is, at least one surface of the elastic housing is provided with convex points, concave-convex stripes, concave-convex patterns or patterns to form the concave-convex surface. The concave-convex surface is easy to process, and can play a good anti-skid effect, thereby preventing the motion detection portion and the finger of the first hand or the finger of the wearable portion from the relative slide.

In some embodiments of the present disclosure, the elastic housing has a long and narrow strip structure, which facilitates setting the motion detection portion on the finger of the first hand so as to detect the motion angle and/or flexion angle of the finger joint.

In some embodiments of the present disclosure, the elastic housing has a length of 10-140 mm.

In some embodiments of the present disclosure, the elastic housing has a length of 10-20 mm and is suitable for children to collect motion information of a single finger joint.

In some embodiments of the present disclosure, the elastic housing has a length of 15-50 mm, which is suitable for children to collect motion information of finger joints of a single finger.

In some embodiments of the present disclosure, the elastic housing has a length of 10-30 mm and is suitable for adults to collect motion information of a single finger joint.

In some embodiments of the present disclosure, the elastic housing has a length of 40-140 mm, and is suitable for adults to collect motion information of finger joints of a single finger, specifically 60 mm, 70 mm, 80 mm, 100 mm or 110 mm, etc.

In some embodiments of the present disclosure, the elastic housing has a longitudinal cross-sectional height of 0.5-6 mm.

In some embodiments of the present disclosure, the elastic housing has a longitudinal cross-sectional height of 6 mm, contributing to increased sensitivity and accuracy of motion information acquisition of the finger joints of the first hand.

In some embodiments of the present disclosure, the longitudinal cross-sectional height of the elastic housing is 0.5 mm, which facilitates the motion detection portion to be attached to the finger.

In some embodiments of the present disclosure, the elastic housing has a longitudinal cross-sectional height of 2 mm, 4 mm, 5 mm, 3.5 mm, or 5.8 mm.

In some embodiments of the present disclosure, the elastic housing has a width of 0.5-12 mm.

In some embodiments of the present disclosure, the elastic housing has a width of 0.5 mm, which facilitates the motion detection portion to be attached to the finger.

In some embodiments of the present disclosure, the elastic housing has a width of 12 mm, which helps to improve the sensitivity and accuracy of motion information acquisition of finger joints of the first hand.

In some embodiments of the present disclosure, the elastic housing has a width of 1 mm, 2 mm, 5 mm, 7 mm, or 10 mm.

In some preferred embodiments of the present disclosure, the elastic housing has a length of 110 mm, a width of 7 mm, and a longitudinal cross-sectional height of 4 mm.

Figure 7:
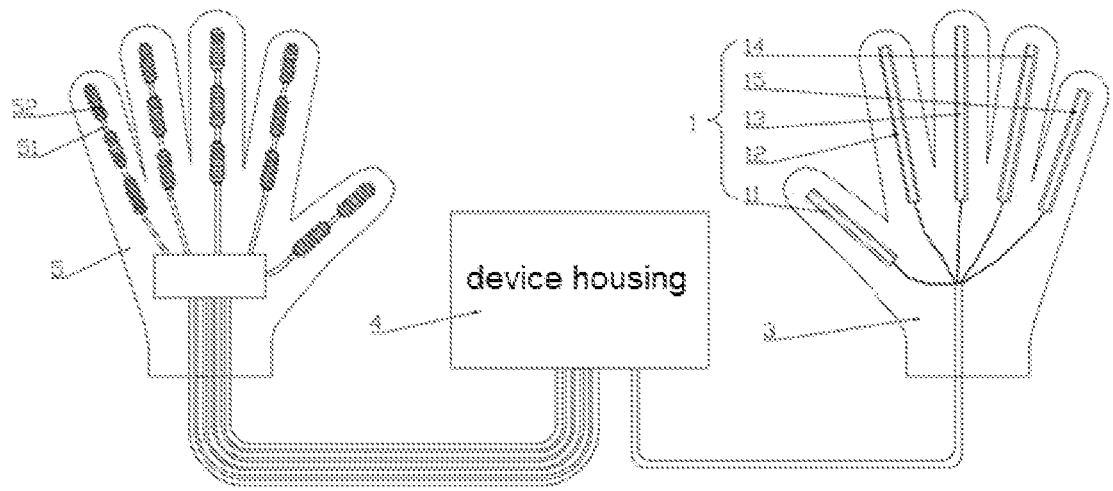
FIG. 7 is a schematic structural diagram of a rehabilitation device in some embodiments of the present disclosure.

FIG. 7 is a schematic structural diagram of a rehabilitation device in some embodiments of the present disclosure.

In some embodiments of the present disclosure, a rehabilitation device is provided, referring to FIG. 7, which includes the hand motion detection device, the hand motion detection device comprises a motion detection portion 1, the motion detection portion is arranged on the finger joint of the first hand and generate detection information for feedback of finger joint movement during the stretching movement and the flexion movement of a finger of the first hand, the rehabilitation device also comprises an air pressure regulating component or assembly (not shown) and a wearable training portion 5, the wearable training portion 5 is provided with a pneumatic adjustable component that can expand and contract freely (not shown), and the air pressure regulating component or assembly (not shown) is connected to the pneumatic adjustable component that can expand and contract freely (not shown) through an air pipe assembly (not shown). The air pressure regulating component (not shown) is connected to the control portion (not shown), and the control portion (not shown) is used to control the air pressure regulating component or assembly (not shown) to regulate the air pressure in the pneumatic adjustable component (not shown) according to the detection information, so that the wearable training portion 5 is changed between the flexion condition and the stretching condition to realize the hand mirror training of the second hand. The condition of the second hand can be regulated by the condition of the first hand, that is, the rehabilitation training time, action and intensity of the second hand can be autonomously regulated by regulating and controlling the motion information collection of the finger joints of the first hand, so that the wearable training portion can be better regulated to meet the training requirements of the second hand. The air pressure regulating component or assembly for driving the movement of the pneumatic adjustable component that can expand and contract freely includes an air pump, a control valve, an air circuit system, etc. The air pressure regulating component or assembly is a conventional means in the art and will not be described here. In some embodiments of the present disclosure, the air pressure regulating component regulates the air pressure within the pneumatic adjustable component that can expand and contract freely by controlling the air pressure regulating component or assembly to inflate or extract air from the pneumatic adjustable component that can expand and contract freely. In other embodiments of the present disclosure, the air pressure regulating component or assembly regulates the air pressure within the pneumatic adjustable component that can expand and contract freely by controlling the amount of air that the air pressure regulating component or assembly inflates to the pneumatic adjustable component that can expand and contract freely, such as by controlling solenoid valves and air passages in the air pressure regulating component or assembly.

In some embodiments of the present disclosure, the control portion is a self-contained component of the rehabilitation device, and the hand motion detection device can be used by connecting with the control portion.

In some embodiments of the present disclosure, referring to FIG. 7, the rehabilitation device further includes a device housing 4, the air pressure regulating component and the control portion are disposed in the device housing 4.

In other embodiments of the present disclosure, the control portion is a self-contained part of the hand motion detection device, and can be used by connecting the control portion with the air pressure regulating component.

In the embodiment of the present disclosure, both the first hand and the second hand are left or right hands of a user, and the mirror training means that the second hand moves with reference to the movement of the first hand.

In some specific embodiments of the present disclosure, the left-hand glove-shaped wearable training portion and the right-hand glove-shaped wearable portion are of a group, and the right-hand glove-shaped wearable training portion and the left-hand glove-shaped wearable portion are of a group. When in use, the wearable portion and the wearable training portion are selected to be electrically connected to the device housing according to the needs of patients.

In some embodiments of the present disclosure, referring to FIG. 7, the wearable training portion 5 is in the shape of a glove, and the pneumatic adjustable component that can expand and contract freely specifically comprises a connecting air pipe 51 and a bellows 52 fixed on the wearable training portion 5 and the air pipe assembly (not shown), and the connecting air pipe 51 and the bellows 52 constitute a set of pneumatic adjustable component that can expand and contract freely (not shown). Each finger of the wearable training portion 5 is provided with a set of pneumatic adjustable component that can expand and contract freely (not shown), and each set of pneumatic adjustable component that can expand and contract freely (not shown) is connected to the air pressure regulating component (not shown) through the air pipe assembly (not shown). The bellows 52 are provided at each joint of the wearable training portion 5, and the adjacent bellows 52 are connected through the connecting air pipe 51. When the bellows 52 is inflated, the air pressure inside the bellows 52 increases, the length of the bellows 52 increases, and the bellows 52 is in a stretched state, so that a finger on which the bellows 52 is provided is bent. When the bellows 52 is pumped, the air pressure inside the bellows 52 decreases, the length of the bellows 52 becomes small, and the bellows 52 is in a compressed state, so that a finger on which the bellows 52 is provided is straightened. In some preferred embodiments of the present disclosure, when the initial state of the wearable training portion is in the stretching condition, when the hand motion detection device just starts, the control portion controls the air pressure regulating component or assembly to extract the air from the pneumatic adjustable component that can expand and contract freely (not shown), the internal air pressure of the bellows 52 decreases, the length of the bellows 52 shortens, and the bellows 52 is in a compressed state, so that the wearable training portion 5 is in the stretching condition, and each finger of the wearable training portion 5 is straightened. At this time, the wearable resistance of the wearable training portion 5 is greatly reduced, and it is convenient for users to wear the wearable training portion 5.

In some embodiments of the present disclosure, the control method of the hand motion detection device includes:
  S1, generating, by a motion detection portion, detection information for feedback of finger joint motion during a stretching movement and a flexion movement of a finger of a first hand, and transmitting the detection information to a control portion; and
  S2, generating, by the control portion, an execution instruction according to the detection information, thereby achieving real-time and accurate acquisition of the motion information of the finger joint of the first hand.

In some embodiments of the present disclosure, a control method of a rehabilitation device is provided, the method includes:
  S1, arranging the motion detection portion on the finger joint of the first hand, and transmitting the detection information to the control portion after the motion detection portion generates the detection information for feedback of finger joint movement during the stretching movement and the flexion movement of the finger of the first hand;

S2, analyzing and processing, by the control portion, the detection information transmitted from the motion detection portion, and generating an execution instruction; and S3, regulating, by the air pressure regulating component, the air pressure in the pneumatic adjustable component that can expand and contract freely according to the execution instruction, so that the wearable training portion is changed between the flexion condition and the stretching condition to realize the hand mirror training of the second hand.

Figure 8:
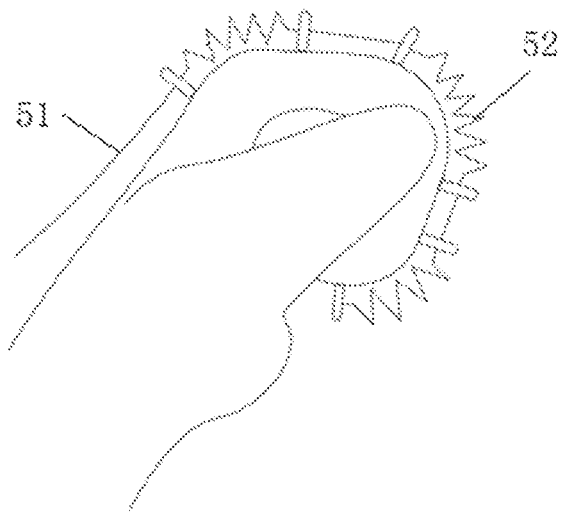
FIG. 8 is a schematic diagram of a wearable training portion in a stretching condition in some embodiments of the present disclosure.
Figure 9:
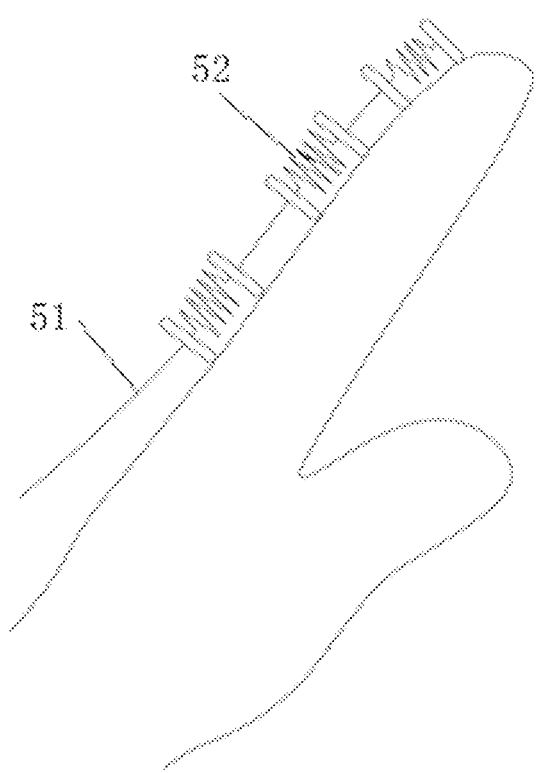
FIG. 9 is a schematic diagram of a wearable training portion in a flexion condition in some embodiments of the present disclosure.

FIG. 8 is a schematic diagram of a wearable training portion in a flexion condition (that is, the bellows 52 are in an elongated state) in some embodiments of the present disclosure. FIG. 9 is a schematic diagram of a wearable training portion in a stretching condition (that is, the bellows 52 are in a compressed state) in some embodiments of the present disclosure.

In some embodiments of the present disclosure, referring to FIG. 7, the user wears the wearable training portion 5 on his left hand and the wearable portion 3 on his right hand. The wearable portion 3 is provided with the hand motion detection device. The hand motion detection device includes a motion detection portion 1, the motion detection portion 1 is arranged on the finger belly back surface of the wearable portion 3. The motion detection portion 1 includes five motion detection portions, namely a first motion detection portion 11, a second motion detection portion 12, a third motion detection portion 13, a fourth motion detection portion 14 and a fifth motion detection portion 15. Each of the motion detection portions is arranged across two (such as thumb) or three (other fingers except thumb) finger joints of a single finger and is respectively connected to the control portion so as to detect the overall motion state of a single finger.

In some specific embodiments of the present disclosure, the index finger movement is taken as an example because the structures of the five fingers are similar. The rehabilitation device is started, and the pneumatic adjustable component that can expand and contract freely on the wearable training portion 5 drives the index finger of the second hand to be in a straightened state. When the index finger of the wearable portion 3 flexes, referring to FIGS. 7 and 8, during the flexing process, the first conductive adhesive layer (not shown) and the second conductive adhesive layer (not shown) in the second motion detection portion 12 contact and conduct with each other to generate detection information and transmit it to the control portion (not shown), and the control portion (not shown) controls the air pressure regulating component or assembly to regulate the pneumatic adjustable component (not shown) on the index finger wearing in the wearable training portion 5 according to the obtained detection information, that is, the air pressure regulating component or assembly controls the internal air pressure of the bellows 52 to increase, and the length of the bellows 52 is elongated and the bellows 52 is in an elongated state, so that the corresponding index finger on the wearable training portion 5 realizes mirror flexing movement. When the index finger of the wearable portion 3 is stretched and the finger joint is in a straightened state, the first conductive adhesive layer (not shown) and the second conductive adhesive layer (not shown) in the second motion detection portion 12 are separated and do not contact with each other, and the control portion (not shown) controls the air pressure regulating component or assembly to regulate the air pressure of the pneumatic adjustable component that can expand and contract freely (not shown) on the index finger wearing in the wearable training portion 5 to decrease, that is, the internal air pressure of the bellows 52 decreases, the length of the bellows 52 shortens and the bellows 52 is in a compressed state, so that the corresponding index finger wearing on the wearable training portion 5 can realize mirror stretching and straightening. That is, the second motion detection portion 12 on the first hand is arranged to fit the index finger to collect the motion information of the finger joint of the index finger so as to realize autonomous control of the index finger of the second hand for mirror training. The principle of mirror training of other fingers is the same. The first motion detection portion 11 on the first hand is arranged to fit the thumb to collect motion information of the finger joint of the thumb so as to realize autonomous control of the thumb of the second hand for mirror training. The third motion detection portion 13 on the first hand is arranged to fit the middle finger to collect the motion information of the finger joint of the middle finger so as to realize autonomous control of the middle finger of the second hand to perform mirror training. The fourth motion detection portion 14 on the first hand fits the ring finger to collect the motion information of the finger joint of the ring finger so as to realize autonomous control of the ring finger of the second hand for mirror training. The fifth motion detection portion 15 on the first hand is arranged to fit the little finger to collect the motion information of the finger joint of the little finger so as to realize autonomous control of the little finger of the second hand for mirror training. Through the hand motion detection device, the user can autonomously control the affected hand to perform rehabilitation action by the healthy hand, to complete mirror training. And the user autonomously stretches and flexes finger joints of the first hand, and finger joints of the second hand are controlled to be stretched and flexed accordingly (i.e., the second hand complete a mirror training), thereby enhancing the participation feeling of the user in treatment and improving the rehabilitation training effect. The motion detection portions do not affect each other and are triggered independently, and the collected detection signals are also independently transmitted to the control portion.

In some embodiments of the present disclosure, the user wears the wearable training portion 5 on his left hand and the wearable portion 3 on his right hand. The wearable portion 3 is provided with the hand motion detection device. The hand motion detection device includes a motion detection portion 1, the motion detection portion 1 is arranged on the finger belly back surface of the wearable portion 3. The motion detection portion 1 includes five motion detection portions, namely a first motion detection portion 11, a second motion detection portion 12, a third motion detection portion 13, a fourth motion detection portion 14 and a fifth motion detection portion 15. Each of the motion detection portions is arranged across two (such as thumb) or three (other fingers except thumb) finger joints of a single finger, so as to detect the overall motion state of a single finger. The first motion detection portion 11, the second motion detection portion 12, the third motion detection portion 13, the fourth motion detection portion 14 and the fifth motion detection portion 15 are connected in series and connected to the control portion by a general wire. Any one of the first motion detection portion 11, the second motion detection portion 12, the third motion detection portion 13, the fourth motion detection portion 14 and the fifth motion detection portion 15 detects the finger joint movement of any finger of the first hand and transmits the collected detection information to the control portion. According to the detection information, the control portion controls the air pressure regulating component or assembly to regulate the air pressure in the pneumatic adjustable component that can expand and contract freely that is arranged on all the fingers of the wearable training portion, so that the wearable training portion is changed between the flexion condition and the stretch condition to realize the hand mirror training of the second hand.

In other specific embodiments of the present disclosure, the user wears the wearable training portion on the left hand and the wearable portion on the right hand, the wearable portion is provided with the hand motion detection device, the hand motion detection device comprises one motion detection portion to detect the joint motion of any finger of the right hand and transmit the collected detection information to the control portion. And according to the detection information the control portion controls the air pressure regulating component to regulate the air pressure in the pneumatic adjustable component that can expand and contract freely arranged on all finger portions of the wearable training portion, so that the wearable training portion is changed between the flexion condition and the stretch condition as a whole, so as to realize the hand mirror training of the second hand, namely, using one motion detection portion arranged on the right hand to control the five fingers of the left hand to carry out the flexion movement and the stretch movement together.

In still other embodiments of the present disclosure, referring to FIG. 3, each finger of the first hand is provided with three motion detection portions, namely the seventh motion detection portion 17, the eighth motion detection portion 18 and the ninth motion detection portion 19, and each of the seventh motion detection portion 17, the eighth motion detection portion 18 and the ninth motion detection portion 19 respectively detect the motion of one finger joint and is respectively connected to the control portion to detect the motion state of a single finger joint. The bellows attached to each finger joint on the wearable training portion are individually connected to the air pressure regulating component or assembly through connecting air pipes, in this way, the control portion controls the corresponding finger joint of the corresponding finger on the second hand to perform mirror training on the receipt of the movement of a single finger joint on a finger of the first hand. For example, the ninth motion detection portion 19 detects the motion information of the metacarpophalangeal joint of the index finger of the first hand, and when the metacarpophalangeal joint of the index finger of the first hand performs the stretching movement and the flexion movement, the ninth motion detection portion 19 generates the detection information and transmits it to the control portion, according to the accepted detection information the control portion controls the air pressure regulating component or assembly to regulate the air pressure in the bellows arranged on the metacarpophalangeal joint of the index finger of the second hand to perform the corresponding stretching movement and flexion movement the same as the first hand, so as to realize mirror training of metacarpophalangeal joints of the index finger of the second hand.

In still other embodiments of the present disclosure, each finger of the first hand is provided with three motion detection portions, i.e., the seventh motion detection portion, the eighth motion detection portion and the ninth motion detection portion, and each of the seventh motion detection portion, the eighth motion detection portion and the ninth motion detection portion respectively detect the motion of one finger joint. The seventh motion detection portion, the eighth motion detection portion and the ninth motion detection portion are connected in series, and are connected to the control portion by a general wire to detect the motion state of a single finger joint. When any one of the seventh motion detection portion, the eighth motion detection portion and the ninth motion detection portion detects the motion of any finger joint of the first hand, a collected detection information is transmitted to a control portion, and according to the detection information the control portion controls the air pressure regulating component to regulate the air pressure in the pneumatic adjustable component or assembly that may be arranged on the finger portions of the wearable training portion, so that the whole wearable training portion is changed between the flexion condition and the stretching condition to realize hand mirror training of the second hand.

In some embodiments of the present disclosure, the control portion converts the detection information into angle value information, and controls the air pressure regulating component to regulate the air pressure output to the pneumatic adjustable component that can expand and contract freely according to the angle value information so as to make the finger of the wearable training portion realize the flexion of the corresponding angle value, and according to the detection information generated by the motion detection portion during the stretching movement and flexion movement of the finger of the first hand, the finger of the wearable training portion can be automatically controlled so as to realize the flexion of the corresponding angle value.

In some embodiments of the present disclosure, the hand motion detection device can collect real-time angle value information of a first hand, and through the real-time angle value information of a first hand, a second hand finger is controlled to perform a mirror training. Referring to FIG. 7, take the index finger movement as an example, when the flexion angle of the index finger joint of the wearable portion 3 changes, accordingly the contact area of the first conductive adhesive layer (not shown) and the second conductive adhesive layer (not shown) in the second motion detection portion 12 changes and generates a detection information, the detection information is transmitted to the control portion (not shown). The control portion (not shown) converts the obtained detection information into the corresponding angle value information and air pressure information, and controls the pressure in the corresponding telescopic component of the wearable training portion 5 through the air pressure regulating component or assembly to change the internal air pressure of the bellows 52. The length of the bellows 52 changes and the flexion angle changes, so that the corresponding index finger on the wearable training portion 5 performs the mirror flexion movement and the flexion angle changes accordingly. In some specific embodiments of the present disclosure, when the metacarpophalangeal joint of the index finger flexes, the contact area of the first conductive adhesive layer (not shown) and the second conductive adhesive layer (not shown) becomes larger, the resistance value between the first and second conductive adhesive layers (not shown) decreases, and the detection information changes. According to the different detection information, the motion information of the finger can be obtained. The control portion (not shown) converts the detection information into the corresponding angle value information and air pressure information, and controls the pressure in the corresponding telescopic component on the index finger of the wearable training portion 5 to increase through the air pressure regulating component or assembly so as to drive the index finger of the wearable training portion 5 to realize the change of the mirror flexion angle. When the metacarpophalangeal joint of the index finger is stretched, the contact area between the first conductive adhesive layer (not shown) and the second conductive adhesive layer (not shown) becomes smaller, the resistance value between the first and second conductive adhesive layer (not shown) increases, and the detection information changes. According to the different detection information, the motion information of the finger can be obtained. The control portion (not shown) converts the detection information into the corresponding angle value information and air pressure information, and controls the pressure in the corresponding telescopic component on the index finger of the wearable training portion 5 to decrease through the air pressure regulating component or assembly so as to drive the index finger of the wearable training portion 5 to realize the change of the flexion angle of the mirror.

In some embodiments of the present disclosure, the control portion controls a start or stop of the wearable training portion according to the detection information, and realizes the self-control of the wearable training portion. According to the detected information that is generated by a motion detection portion during the stretching movement and flexion movement of the fingers of the first hand, the wearable training portion is autonomously controlled to start. According to the detected information that is generated by a motion detection portion during the straightening of the fingers of the first hand, the wearable training portion is autonomously controlled to stop.

In some embodiments of the present disclosure, one finger joint of the first hand is provided with one motion detection portion. According to the detected information that is generated by the motion detection portion during the stretching movement and flexion movement of the finger joint of the first hand of a user, the wearable training portion is controlled to start by the user. According to the detected information that is not generated by the motion detection portion at the time when the finger joint of the first hand of a user is straightened, the wearable training portion is controlled to stop by the user.

In some embodiments of the present disclosure, through a key portion on a device housing a user can set a training mode that the motion detection portions on a plurality of fingers of the first hand can serve as control switches for the movement of the wearable training portion, that is, the user wears the wearable training portion in a passive training mode. In a passive training mode, the user can control the wearable training portion to start the movement by the plurality of motion detection portions on the first hand generating the detection information during the stretching movement and flexion movement of the fingers of the first hand. In a passive training mode, the user can control the wearable training portion to stop the movement by the plurality of motion detection portions on the first hand not generating detection information when the fingers of the first hand are straightened.

In some embodiments of the present disclosure, through a key portion on a device housing the user can set a training mode that motion detection portions on one certain finger of the first hand serve as control switches for the movement of the wearable training portion, that is, the user wears the wearable training portion in an another passive training. In the another passive training, the user can control the wearable training portion to start the movement by the motion detection portion on the finger of the first hand generating the detection information during the stretching movement and flexion movement of the finger of the first hand. In the another passive training, the user can control the wearable training portion to stop the movement by the motion detection portion on the finger of the first hand not generating detection information when the finger of the first hand is straightened.

In some embodiments of the present disclosure, an autonomous control system is provided, which comprises an executing portion and a hand motion detection device, the executing portion is connected to the control portion, the executing portion is used for moving according to the execution instruction.

In some embodiments of the present disclosure, the executing portion comprises a driving unit for driving an image to move or a sound to change or a game to run according to a motion execution instruction, the image, the sound and the game stored in a terminal device, the executing portion drives the image to move or a sound to change or a game to run according to the execution instruction, so that the user can autonomously regulate the collection of the motion information of the finger joints of the first hand according to the feedback result to carry out the hand autonomous training, the flexibility of the autonomous training is higher, the actual situation of the user is more appropriate, and the training effect is improved. Moreover, by driving the image to move or the sound to change or the game to run to feedback the motion information of the finger joints of the first hand, the user can get the training feedback result in real time, the training effect is more intuitive, and the completion degree of the hand action of the patient can be accurately reflected, and driven by the fun of the game, the user is willing to carry out autonomous training, the training compliance is high, and the training effect is improved.

In some embodiments of the present disclosure, the terminal device has game software stored in it, the terminal device is connected to said control portion, a finger of the first hand of the user is provided with three motion detection portions, i.e., the seventh motion detection portion, the eighth motion detection portion and the ninth motion detection portion, and are connected to the control portion respectively. The seventh motion detection portion fits the distal interphalangeal joint and generates detection information during the stretching movement and flexion movement of the distal interphalangeal joint to collect the motion information of the distal interphalangeal joint. The eighth motion detection portion fits the proximal interphalangeal joint, and the eighth motion detection portion generates the detection information during the stretching movement and flexion movement of the proximal interphalangeal joint to collect the motion information of the proximal interphalangeal joint. The ninth motion detection portion fits the metacarpophalangeal joints, and the ninth motion detection portion generates detection information during the stretching and flexing movements of the metacarpophalangeal joints so as to collect motion information of the metacarpophalangeal joints. When the metacarpophalangeal joint makes the flexion movement, the first conductive adhesive layer and the second conductive adhesive layer in the ninth motion detection portion contact and conduct with each other to generate the resistance value information with the gradually decreasing resistance value and is transmitted to the control portion, and the control portion controls the characters in the game to move left. When the metacarpophalangeal joint makes the stretching movement, the first conductive adhesive layer and the second conductive adhesive layer in the ninth motion detection portion contact and conduct with each other so as to generate resistance value information with gradually increasing resistance value, which is transmitted to the control portion, and the control portion controls the characters in the game to move right. Similarly, when the proximal interphalangeal joint makes the flexion movement, the control portion controls characters in the game to move up. When the proximal interphalangeal joint makes the stretching movement, the control portion controls characters in the game to move down. When the distal interphalangeal joint makes the flexion movement, the control portion controls characters in the game to crawl. When the distal interphalangeal joint makes the stretching movement, the control portion controls characters in the game to jump, and the control portion controls characters in the game to move according to a change amount of the resistance value. In some preferred embodiments of the present disclosure, the motion detection portions that are arranged on a plurality of fingers of a user are provided with, and the motion detection portions are respectively connected to the control portions, and the control portions control different actions of characters in the game according to the detection information of the motion detection portions on each finger. In other preferred embodiments of the present disclosure, a plurality of fingers of the user are provided with the motion detection portions, and each finger is provided with a plurality of the motion detection portions to detect the motion of a single finger joint, and the motion detection portions are respectively connected to the control portions so that the control portions respectively control more actions of characters in the game.

In some embodiments of the present disclosure, when performing autonomous training, for a user whose hand is seriously injured and cannot freely stretch and bend, the wearable training portion can be worn on the hand and an air pressure regulating component or assembly connected to the wearable training portion can be arranged to assist autonomous training, that is, the motion detection portion and the pneumatic adjustable component can be arranged on the same glove at the same time.

While the embodiments of the present disclosure have been described in detail, it will be apparent to those skilled in the art that various modifications and variations can be made to the embodiments. However, it is to be understood that such modifications and variations are within the scope and spirit of the present disclosure as described in the appended claims. Furthermore, the present disclosure described herein is susceptible to other embodiments and may be embodied or carried out in various ways.

The invention claimed is:

1. A hand motion detection device comprising: a motion detection portion adapted to be arranged on a finger joint of a first hand and configured for generating detection information for feedback of finger joint movement during a stretching movement and a flexion movement of a finger of the first hand, the motion detection portion being connected to a control portion, the motion detection portion configured for transmitting the detection information to the control portion, and the control portion adapted to generate an execution instruction according to the detection information,
wherein the motion detection portion comprises a first detection unit and a second detection unit adapted to be arranged separately;
wherein the first detection unit comprises a first conductive adhesive layer, the second detection unit comprises a second conductive adhesive layer, the first conductive adhesive layer and the second conductive adhesive layer are respectively arranged on opposite inner side walls of an elastic housing and spaced apart from each other so as to define a void space where no element is accommodated therein at a non-flexion state, and when the finger joint of the first hand is in a flexion state, a bottom face of the first conductive adhesive layer is configured to abut against an upper face of the second conductive adhesive layer to generate the detection information.

2. The hand motion detection device according to claim 1, wherein the motion detection portion is adapted to be provided across at least one finger joint, and the detection information is generated during a stretching movement and a flexion movement of the at least one finger joint.

3. The hand motion detection device according to claim 1, wherein the motion detection portion is adapted to be provided on at least one finger of the first hand, and a single finger is provided with at least one motion detection portion.

4. The hand motion detection device according to claim 1, wherein several motion detection portions is adapted to be provided on the finger joint.

5. The hand motion detection device according to claim 1, further comprising a wearable portion, the wearable portion being in a shape of a glove and comprising a finger portion, and the motion detection portion is arranged on the finger portion.

6. The hand motion detection device according to claim 5, wherein the finger portion is provided with an accommodating portion, and the motion detection portion is arranged within the accommodating portion.

7. The hand motion detection device according to claim 5, wherein the motion detection portion is fixed to the finger portion by any one of glue, a hook and loop fastener, a magnet, a stitch, a buckle, a finger cuff and a strap.

8. The hand motion detection device according to claim 1, wherein the first conductive adhesive layer and the second conductive adhesive layer are made of conductive adhesive.

9. The hand motion detection device according to claim 1, wherein each of the first conductive adhesive layer and the second conductive adhesive layer comprises a conductive adhesive and a wire embedded in the conductive adhesive.

10. The hand motion detection device according to claim 9, wherein the control portion and the motion detection portion are electrically connected by the wire.

11. The hand motion detection device according to claim 8, wherein one end of the elastic housing is further provided with a conductive element, upper and lower end faces of the conductive element are respectively in contact with the first conductive adhesive layer and the second conductive adhesive layer, and the control portion and the motion detection portion are electrically connected by the conductive element.

12. A control method of the hand motion detection device according to claim 1, the method comprising:
S1, generating, by the motion detection portion, detection information for feedback of finger joint motion during a stretching movement and a flexion movement of a finger of a first hand, and transmitting the detection information to the control portion; and
S2, generating, by the control portion, the execution instruction according to the detection information.

13. A rehabilitation device comprising the hand motion detection device adapted for collecting detection information according to claim 1, wherein the rehabilitation device further comprises an air pressure regulating assembly and a wearable training portion, the wearable training portion is provided with a pneumatic adjustable component that is adapted to expand and contract freely, and the air pressure regulating assembly is connected to the pneumatic adjustable component that is adapted to expand and contract freely; and the air pressure regulating assembly is connected to the control portion, and the control portion is configured for controlling the air pressure regulating assembly to regulate air pressure in the pneumatic adjustable component that is adapted to expand and contract freely according to the detection information, such that the wearable training portion is changed between a flexion condition and a stretching condition to achieve hand mirror training of a second hand.

* * * * *